(12) United States Patent
Mack et al.

(10) Patent No.: US 6,930,216 B2
(45) Date of Patent: Aug. 16, 2005

(54) METHOD FOR THE NUCLEAR CHLORINATION OF ORTHO-XYLENE

(75) Inventors: Karl-Ernst Mack, Wiesbaden (DE); Hans-Jürgen Leitung, Frankfurt (DE); Daniel Decker, Liederbach a. Ts (DE)

(73) Assignee: Clariant GmbH, Frankfurt (DE)

( * ) Notice: Subject to any disclaimer, the term of this patent is extended or adjusted under 35 U.S.C. 154(b) by 1 day.

(21) Appl. No.: 10/659,590

(22) Filed: Sep. 10, 2003

(65) Prior Publication Data

US 2004/0054239 A1 Mar. 18, 2004

(30) Foreign Application Priority Data

Sep. 12, 2002 (DE) .......................... 102 42 224

(51) Int. Cl.$^7$ .......................... C07C 17/12; C07C 25/00
(52) U.S. Cl. .......................... 570/209; 570/208; 570/210
(58) Field of Search ............................... 570/208, 209, 570/210

(56) References Cited

U.S. PATENT DOCUMENTS

| | | | |
|---|---|---|---|
| 4,190,609 A | 2/1980 | Lin | 260/650 R |
| 4,289,916 A | 9/1981 | Nakayama et al. | 570/209 |
| 4,444,983 A | 4/1984 | Hattori et al. | 570/209 |
| 4,647,709 A | 3/1987 | Wolfram | 570/209 |
| 5,095,157 A * | 3/1992 | Mais et al. | 568/940 |
| 5,177,268 A | 1/1993 | Balko et al. | 568/726 |
| 5,552,549 A | 9/1996 | Rasp et al. | 546/139 |
| 5,621,153 A * | 4/1997 | Krishnamurti et al. | 570/209 |
| 5,625,110 A | 4/1997 | Schoedel et al. | 585/641 |
| 2002/0049357 A1 | 4/2002 | Mais | 570/237 |

FOREIGN PATENT DOCUMENTS

| | | |
|---|---|---|
| EP | 0 126 669 | 11/1984 |
| EP | 0 173 222 | 3/1986 |
| WO | WO 02/14245 | 2/2002 |

OTHER PUBLICATIONS

Ullmann's Encyclopedia of Industrial Chemistry, 5$^{th}$ ed., vol. A6, p. 343 (1995).
English abstract for EP 0126669, Nov. 28, 1984.
Ullmann's Encyclopadia of Industrial Chemistry, 5th edition, vol. A8, pp. 211–215.
"Selective para chlorination of o–Xylene over zeolite catalysts", Journal of Catalysls, 150, 1994, pp. 430–433.
Sudip Mukhopadhyay et al., "Palladium–catalyzed Aryl–Aryl coupling in water using molecular hydrogen: kinetics and process optimization of a solid–liquid–gas system", Tetrahedron, 55, 1999, pp. 14763–14768.
Chemical abstract, CA 1998, Nr. 472737.
Chemical abstract, CA 1991, Nr. 514135.

\* cited by examiner

*Primary Examiner*—Rosalynd Keys
(74) *Attorney, Agent, or Firm*—Richard P. Silverman

(57) ABSTRACT

A method for the nuclear chlorination of ortho-xylene using a chlorinating agent in the presence of at least one Friedel-Crafts catalyst and chloro-substituted 2,8-dimethylphenoxathiin as co-catalyst. The co-catalyst used is preferably tetrachlorinated 2,8-dimethylphenoxathiin, in particular 1,3,7,9-tetrachloro-2,8-dimethylphenoxathiin of the formula

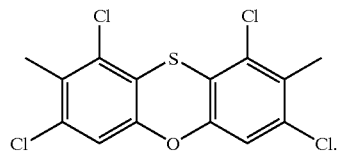

15 Claims, No Drawings

METHOD FOR THE NUCLEAR CHLORINATION OF ORTHO-XYLENE

The present invention relates to a method for the nuclear chlorination of ortho-xylene to give an isomer mixture of 4-chloro-1,2-dimethylbenzene and 3-chloro-1,2-dimethylbenzene in the presence of a catalyst and a co-catalyst.

Mononuclear chlorinated ortho-xylenes are valuable intermediates for preparing active agricultural and pharmaceutical compounds.

The nuclear chlorination of ortho-xylene is known and is customarily performed in the presence of Friedel-Crafts catalysts, for example Fe, $FeCl_3$, $SbCl_3$ or $SbCl_5$. The mononuclear chlorination produces in this manner a mixture of 4-chloro- and 3-chloro-isomers in a ratio of less than 1.5:1 (U.S. Pat. No. 4,190,609). Since the 4-chloro-isomer is the more valuable of the two, a plurality of processes are described to increase its proportion.

By adding simple sulfur compounds as co-catalyst, the proportion of 4-chloro-1,2-dimethylbenzene can be increased, for example by using $Fe+S_2Cl_2$, to a ratio of the 4-chloro-isomer to the 3-chloro-isomer of 1.78:1 (Chemical Abstracts CA 1988, No. 472737).

U.S. Pat. No. 4,190,609 discloses a method for the nuclear chlorination of ortho-xylene, which comprises working in the presence of Lewis acids as catalysts and certain substituted thianthrenes as co-catalysts. Although this increases the ratio of the 4-chloro-isomer to the 3-chloro-isomer to 3.81:1, a disadvantage in the use of the thianthrenes is that these compounds must be rated as highly toxic, similar to dioxins.

EP-A-126 669 describes the nuclear chlorination of ortho-xylene using $SbCl_3$ and N-chlorocarbonylphenothiazine as co-catalyst, in which a ratio of 4-chloro-isomer to 3-chloro-isomer of 2.3:1 is achieved.

WO 02/14245 describes substituted benzo-condensed thiazepines or thiazocines as co-catalysts for the chlorination of ortho-xylene in the presence of Lewis acids. High-activity co-catalysts of these classes of compounds which lead to ratios of 4-chloro-isomer to 3-chloro-isomer of greater than 3:1, however, require complicated substitution patterns which are demanding to prepare.

A fundamentally different method for the nuclear chlorination of ortho-xylene is the use of heterogeneous catalysts, for example zeolites. Thus, Chemical Abstracts CA 1991, No. 514135 reports a ratio of 4-chloro-isomer to 3-chloro-isomer of 3.87:1 by using a KL-zeolite in nitrobenzene as solvent. In J. Catal. 150, 1994, 430–433, although an isomer ratio of 11.73:1 is achieved using the special solvent 1,2-dichloroethane, the conversion rate of ortho-xylene is only 60.6%. A disadvantage of the use of zeolites is the requirement for filtration, and, because of the use of solvents, recovery thereof by distillation.

It was an object of the present invention to provide a method for the nuclear chlorination of ortho-xylene using a catalyst system which is simple to handle, in which a very high ratio of 4-chloro- to 3-chloro-1,2-dimethylbenzene is to be achieved which is at least 3:1.

The object set is surprisingly achieved by using chlorine-substituted 2,8-dimethylphenoxathiin as co-catalyst.

The invention thus relates to a method for the nuclear chlorination of ortho-xylene in the presence of a Friedel-Crafts catalyst with addition of chlorinated, in particular tetrachlorinated, if appropriate substituted, 2,8-dimethylphenoxathiin.

The chlorination agent used in this case is, for example, sulfuryl chloride or elemental chlorine. A preferred chlorination agent is elemental chlorine.

Suitable Friedel-Crafts catalysts for the inventive method are known from textbooks. Examples which may be mentioned are: antimony chlorides, aluminum chlorides, iron chlorides, molybdenum chlorides, titanium chlorides, tungsten chlorides, tin chlorides, zinc chlorides or boron trihalides, to name only a few.

Elements or compounds of elements which form a Friedel-Crafts catalyst during the chlorination can also be used, for example oxides or salts, such as carbonates or sulfides, and also other halides, such as fluorides, bromides or if appropriate iodides.

Preferably, antimony chlorides, iron, iron oxides, iron sulfides and iron(III) chloride are used in the inventive method. Particular preference is given to iron(III) chloride.

In a very preferred embodiment, iron is used, for example in the form of rings, from which the active Friedel-Crafts catalyst forms when chlorine flows through them.

Friedel-Crafts catalysts and/or precursors thereof can be used individually or as any mixtures with one another, the amount based on the ortho-xylene used being able to vary within broad limits from 0.0005 to 5% by weight. Usually, amounts of from 0.001 to 1% by weight are sufficient, preference is given to 0.005 to 0.5% by weight. When iron rings are used, a dissolved iron content in the reaction solution of 0.004% by weight is found, for example.

In the inventive method, the co-catalyst preferably used is tetrachlorinated 2,8-dimethylphenoxathiin. Its preparation and characterization is described in detail in EP-A-0 173 222. There, it is set forth that the co-catalyst principally consists of 1,3,7,9-tetrachloro-2,8-dimethylphenoxathiin of the formula

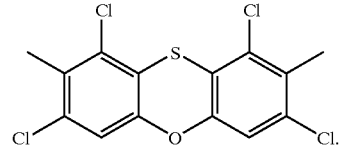

The inventive co-catalyst can be used in the broad quantitative range from 0.001 to 5% by weight. However, expediently, a quantitative range from 0.001 to 1% by weight is used, preferably from 0.01 to 0.5% by weight, based on the ortho-xylene used.

The weight ratio of Friedel-Crafts catalysts or precursors thereof to the co-catalyst can be varied in the inventive method in broad limits. A suitable ratio of Friedel-Crafts catalysts or precursors thereof to the co-catalyst is, for example, from 500:1 to 1:5, preferably from 10:1 to 1:3, particularly preferably from 10:2.5 to 1:2.

The inventive method can be carried out in dilution with a solvent. Suitable solvents are those which are not attacked under the nuclear-chlorination conditions, for example methylene chloride, chloroform, carbon tetrachloride or acetic acid. However, preference is given to working without solvent.

The amount of the chlorinating agent used can be selected so that a degree of chlorination of significantly greater than 1 results. It is found in this case, surprisingly, that with an increasing degree of chlorination above 1, the ratio of 4-chloro-1,2-dimethylbenzene to 3-chloro-1,2-dimethylbenzene can be considerably increased. For example, in the case of the preferred chlorination using chlorine at a degree of chlorination of 1.3, a surprisingly extremely high ratio of 5.6:1 is achieved.

The nuclear chlorination carried out according to the invention can in principle be performed as a method in the liquid phase in the broad temperature range of the liquid state of ortho-xylene and, when a solvent is used, in the temperature range of the liquid state of the mixture of ortho-xylene and the solvent. Generally, with decreasing temperature of the reaction, a slight improvement of the ratio of the 4-chloro-isomer to 3-chloro-isomer may be observed. The temperature range for the reaction is generally expediently at from −20 to 120° C., preferably at from −5 to 90° C., particularly preferably at from 0 to 60° C.

The reaction pressure can be atmospheric pressure, reduced pressure or elevated pressure, and is not in principle critical. Preferably for equipment reasons, atmospheric pressure is employed.

The water content of the reaction mixture is generally not critical and therefore the use of specially dried starting materials is not required. However, it is expedient, for example for reasons of corrosion because of the hydrogen chloride released during the reaction, to have target water contents in the reaction mixture of less than 200 ppm.

For the procedure of the inventive method, the sequence of addition of the individual components to the reaction mixture can be optional.

The method can be carried out either batchwise or continuously. In the batchwise procedure, for example, ortho-xylene is charged, Friedel-Crafts catalyst or a precursor, for example iron rings, and co-catalyst are added and, after setting the desired reaction temperature, the chlorinating agent, preferably chlorine, is added. In the case of the continuous procedure, after a batchwise initiating reaction, in the same manner and simultaneously ortho-xylene, which contains, dissolved, the two catalyst types, and chlorine are added. The continuous procedure can be performed in the reactors which are generally known therefor, such as flow tube, circulation reactor, vessel cascade or bubble-column. Preferably, in the continuous reaction, a bubble-column is employed, in which, for example, the reaction mixture flows through a bed of iron rings, forming the Friedel-Crafts catalyst continuously in situ.

The chlorination mixture can be worked up directly by distillation. The co-catalyst remaining in the bottom phase can, if required, be recovered therefrom.

The inventive method permits the nuclear chlorination of ortho-xylene having high proportions of 4-chloro-1,2-dimethylbenzene using very small amounts of Friedel-Crafts catalyst and co-catalyst and simple workup of the reaction mixture by direct distillation. The ratio of the 4-chloro-isomer to the 3-chloro-isomer is at least 3:1 and can be increased by selecting the degree of chlorination greater than 1, for example can be increased to 5.6:1 at a degree of chlorination of 1.3.

The examples below illustrate the inventive method, without limiting it thereto, however.

EXAMPLE 1

6784 g (64 mol) of ortho-xylene are placed in a jacketed vessel having an inner diameter of 15 cm and a height of 90 cm and 3.4 g of co-catalyst are dissolved therein, and 4544 g (64 mol) of chlorine are introduced via a glass frit at the bottom of the reactor at 20° C. in the course of 5 hours. Around the glass frit is located a bed of iron rings. After a short saturation phase of the reactor contents with chlorine, the vigorous release of hydrogen chloride begins with simultaneous heating; the solution is held at 20° C. by cooling.

After the reaction is complete, a dissolved iron content of 35 ppm is found. Gas-chromatographic analysis of the reaction mixture found 6.9% of ortho-xylene, 65.6% of 4-chloro-1,2-dimethylbenzene, 21.4% of 3chloro-1,2-dimethylbenzene, 5.5% of dichlorinated ortho-xylene and 0.3% of high-boilers. The ratio of 4-chloro-isomer to 3-chloro-isomer is 3.06.

EXAMPLE 2

In a glass flask equipped with stirrer and a gas introduction tube, 2 mol of ortho-xylene are admixed with 0.2 g of $FeCl_3$ and 0.2 g of co-catalyst, cooled to −5° C. and treated with 2.25 mol of chlorine gas (degree of chlorination 1.125) in the course of 2.5 hours with stirring. Gas-chromatographic analysis showed complete conversion of ortho-xylene and found 70.1% of 4-chloro-1,2-dimethylbenzene, 18.9% of 3-chloro-1,2-dimethylbenzene and 11% of di- and higher-chlorinated ortho-xylene. The ratio of 4-chloro-isomer to 3-chloro-isomer is 3.7.

EXAMPLE 3

Similarly to the method in Example 2, the reaction is carried out at 7° C. and a degree of chlorination of 1.3 is selected. Gas-chromatographic analysis found 61.2% of 4-chloro-1,2-dimethylbenzene and 10.8% of 3-chloro-1,2-dimethylbenzene and thus gives a ratio of the 4-chloro-isomer to the 3-chloro-isomer of 5.66.

What is claimed is:

1. A method for the nuclear chlorination of ortho-xylene, which comprises reacting ortho-xylene with a chlorinating agent in the presence of at least one Friedel-Crafts catalyst and chlorine-substituted 2,8-dimethylphenoxathiin as co-catalyst, wherein the ratio of 4-chloro- to 3-chloro-1,2-dimethylbenzene is at least 3:1.

2. The method as claimed in claim 1, wherein tetrachlorinated 2,8-dimethylphenoxathiin is used.

3. The method as claimed in claim 1, wherein elemental chlorine or sulfuryl chloride is used as chlorinating agent.

4. The method as claimed in claimed in claim 1, wherein the co-catalyst is used in an amount of from 0.001 to 5% by weight, based on the amount of the ortho-xylene used.

5. The method as claimed in claim 1, wherein the ratio of Friedel-Crafts catalyst or its precursor to the co-catalyst is in the range from 500:1 to 1:5.

6. The method as claimed in claim 1, wherein the method is carried out without addition of a solvent.

7. The method as claimed in claim 1, wherein the method is carried out at a temperature in the range from −20 to +120° C.

8. The method as claimed in claim 1, wherein the amount of the chlorinating agent used is selected such that a degree of chlorination of significantly greater than 1 results.

9. The method as claimed in claim 2, wherein 1,3,7,9-tetrachloro-2,8-dimethylphenoxathiin of the formula

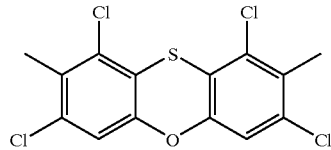

is used.

10. The method as claimed in claim 2, wherein elemental chlorine or sulfuryl chloride is used as chlorinating agent.

11. The method as claimed in claim 2, wherein the co-catalyst is used in an amount of from 0.001 to 5% by weight, based on the amount of the ortho-xylene used.

12. The method as claimed claim 2, wherein the ratio of Friedel-Crafts catalyst or its precursor to the co-catalyst is in the range from 500:1 to 1:5.

13. The method as claimed claim 3, wherein the method is carried out without addition of a solvent.

14. The method as claimed in claim 3, wherein the method is carried out at a temperature in the range from −20 to +120° C.

15. The method as claimed in claim 3, wherein the amount of the chlorinating agent used is selected such that a degree of chlorination of significantly greater than 1 results.

* * * * *